United States Patent [19]

Acquanetta

[11] Patent Number: 4,580,980
[45] Date of Patent: Apr. 8, 1986

[54] DENTURE FOR REDUCING THE COSMETIC EFFECT OF FACIAL AGE LINES

[76] Inventor: Acquanetta, 4415 N. Arcadia La., Phoenix, Ariz. 85018

[21] Appl. No.: 685,558

[22] Filed: Dec. 24, 1984

[51] Int. Cl.⁴ ............................................. A61C 13/00
[52] U.S. Cl. ..................................................... 433/167
[58] Field of Search ....................... 433/167, 171, 172

[56] References Cited

U.S. PATENT DOCUMENTS

| | | | |
|---|---|---|---|
| 994,213 | 6/1911 | Supplee | 433/172 |
| 1,226,382 | 5/1917 | Robertson | 433/172 |
| 1,417,345 | 5/1922 | Pimienta | 433/172 |

OTHER PUBLICATIONS

"Helpful Hints for Special Problems" pp. 9 and 13.
"Dentures for a Severe Class III Jaw Relationship" Hallam, *Journal of Dentistry*, 4, No. 6, 1976, pp. 291–292.
"The Maxillary Denture Labial Flange", Ludwig, South Carolina Dental Journal 29.

*Primary Examiner*—John J. Wilson
*Attorney, Agent, or Firm*—M. David Shapiro

[57] ABSTRACT

The invention comprises an improvement to an artificial denture, in the preferred embodiment, which provides support for age line features on the face of the wearer of the denture. The support mechanism comprises protuberances molded into the gum area of the denture to stretch the overlying skin tissue which carries the age lines and to urge those age lines into a more youthful configuration.

2 Claims, 6 Drawing Figures

U.S. Patent    Apr. 8, 1986    4,580,980
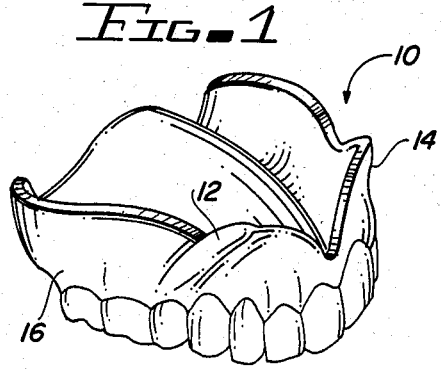
FIG-1
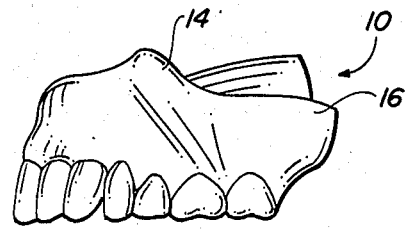
FIG-4
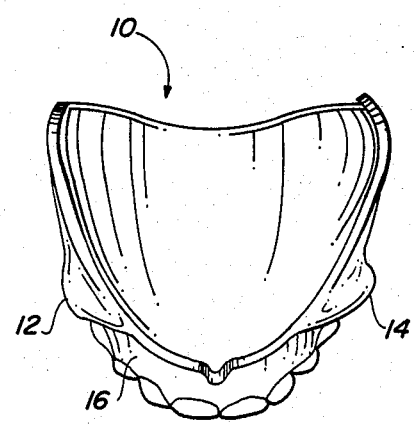
FIG-2
FIG-5
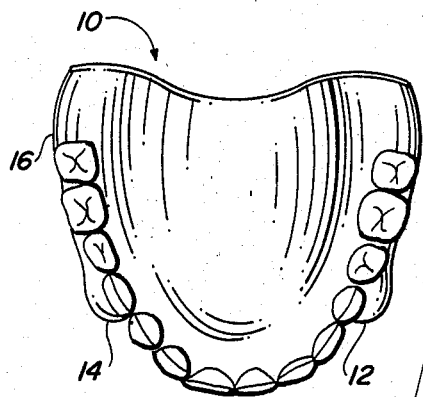
FIG-3
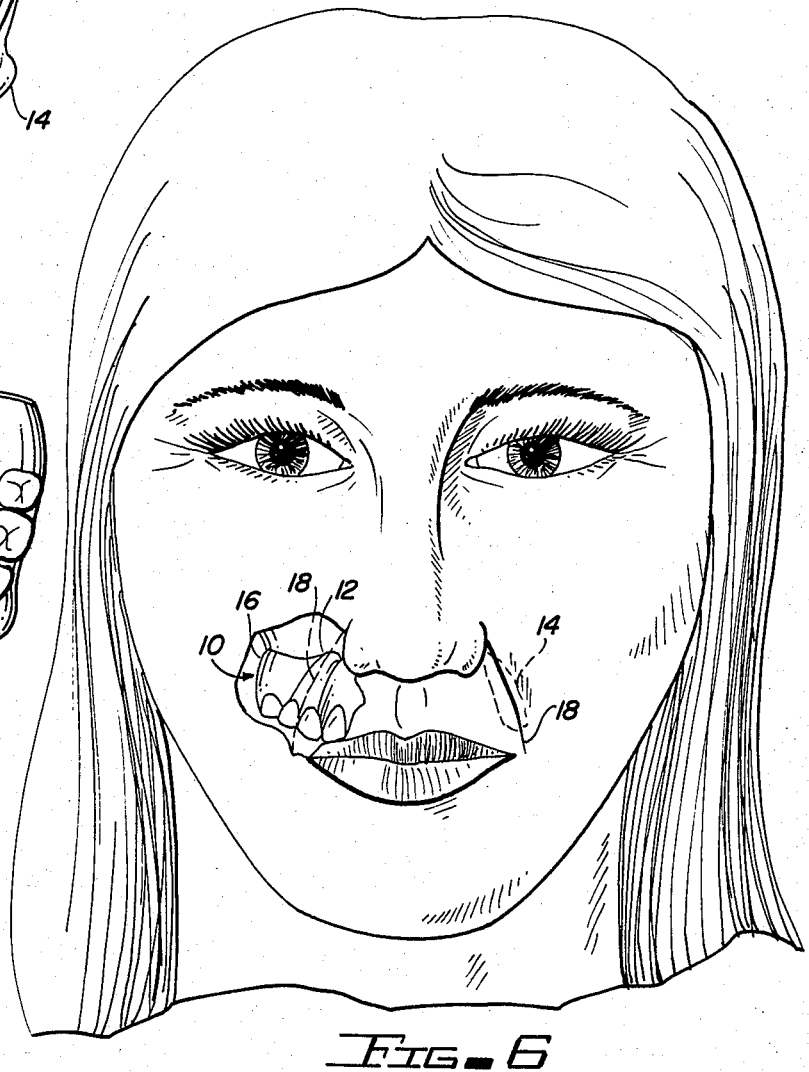
FIG-6 ically as a feature installed in the upper

DENTURE FOR REDUCING THE COSMETIC EFFECT OF FACIAL AGE LINES

FIELD OF THE INVENTION

The invention relates to an improvement in a denture to provide an improved facial appearance for persons afflicted by age lines or other depressed portions of their facial features.

BACKGROUND OF THE INVENTION

It is well known that as persons age, they develop, to one degree or another, age lines or depressions which become more or less prominent parts of their facial features and are generally considered undesirable in appearance. It is believed that the age lines are caused by a natural loss of collegen from the skin tissue, but it is not necessary to the understanding of the instant invention to establish that as a scientific fact. The deepest age lines generally develop overlying the orbicularis oris muscle (the muscle surrounding the lips which allows "puckering"). These lines run generally from a point adjacent a nostril to a point in the vicinity of the corner of the mouth on the same side of the face.

A "plumper", an outward distortion of the frontal upper gum area of a denture, has been used to compensate for loss of material in the upper jaw bone in elderly patients who wear dentures. This bone loss is believed to be fairly common in older persons who wear artificial dentures and the effect of the plumper is to restructure the outer skin tissue to its earlier configuration so that it does not sag inward toward the anterior upper jaw. The plumper is typically a feature installed in the upper denture gum area above and between the upper canine teeth.

Various creams, lotions and skin conditioners are available which are purported to reduce or eliminate the negative aspects of the appearance of these age lines. However, invariably, they must be applied continually and there is certainly no immediate effect. In many cases application is messy and the long term effect is de minimus at best and not noticeable at worst.

SUMMARY OF THE INVENTION

The instant invention resolves many of the problems inherent in previously used treatments for facial age lines which lie in an area overlying a wearer's artificial dentures. In accordance with the invention, a protuberance is designed into the denture underlying the facial line or depression so that when the denture is worn in its normal position in the wearer's or user's mouth, the protuberance provides an advantageous means for stretching and urging the skin tissue containing the age line outwardly from its normal depressed position, thus reducing or eliminating the negative aspects of the cosmetic appearance of the age line. The effect is immediate and experience has shown that only a short time period is required for the wearer of the improved denture to accommodate to the feel of it in the wearer's mouth. In many cases, new patients for dentures have already developed age lines which run from a point adjacent a nostril to a corner of the mouth since both the requirement for dentures and the development of age lines are generally (with obvious exceptions, of course) a function of ageing.

It is, therefore, an object of the invention to provide improvement in the facial appearance of a person having developed facial age lines or other facial depressions by utilizing the improved denture of the invention.

It is another object of the invention to provide instantaneous improvement in the facial appearance of a person who wears dentures.

These and other advantages of the invention will become more readily understood upon review of the Detailed Description of the Invention, below, together with the drawings as described briefly here:

FIG. 1 is illustrative of a perspective view of the preferred embodiment of the improved upper denture of the invention, as equipped with protuberances intended to underly facial age lines lying between a nostril and a corresponding corner of the mouth of the user;

FIG. 2 is a top view of the denture of FIG. 1;

FIG. 3 is a bottom view of the denture of FIG. 1;

FIG. 4 is a left side view of the denture of FIG. 1;

FIG. 5 is a front view of the denture of FIG. 1; and

FIG. 6 is a frontal view of a denture user with a portion of the cheek area cutaway showing the improved denture in its normal position in the wearer's mouth.

DETAILED DESCRIPTION OF THE INVENTION

Looking first at FIG. 6, it may be seen that the person shown there has developed age lines 18, generally in a line beginning at an outer edge of each nostril and running to a point generally in the vicinity of the corner of the mouth on the same side of her face. (It will be understood that the gender is not important; the invention could as well be applied for use by a man.)

FIGS. 1-5 show a preferred embodiment of the improved upper artificial denture 10 of the invention as it is fabricated to provide an improvement in appearance with respect to age lines 18 in FIG. 6. Protuberances 12 and 14 are located on denture 10 on the right and left side thereof, respectively, so that they exactly underly age lines 18 (FIG. 6) when denture 10 is positioned in its normal location within the mouth of the wearer. Protuberances 12 and 14 may typically be located immediately above and between the first bicuspid and the second molar and are shaped, generally, as shown. Of course, it must be understood that the precise position, angle and shape are specific to a given user. It should also be understood that protuberances 12 and 14 are provided by a shaping of gum area 16 of denture 10 and that this shaping is well within the skill of the average practicing dentist.

In the first "try in" model of a denture, a roll of wax may be placed on the denture in the correct location and shaped to provide the support and stretch of the age line area which is desired to meet the needed end result. An advantage that is inherent in this procedure is that the patient has an immediate "preview" of the cosmetic effect that the improvement will have on his or her appearance and there is an opportunity for the patient to advise the denturist as to the patient's desire to lessen or increase that cosmetic effect.

I have referred to protuberances 12 and 14, as incorporated in an upper denture to reduce facial age line effects as shown in the drawings, as "greater wings".

While the preferred embodiment of the invention is described herein, it would clearly be possible to provide the relevant protuberant features 12 and 14 of the invention to the sort of flange typically used in the treatment of periodontal disease and there may well be other such devices which would be adaptable to application of these features.

While the invention has been particularly shown and described with reference to a preferred embodiment thereof, it will be understood by one of ordinary skill in the art that various other modifications and changes may be made to the present invention from the principles of the invention described above without departing from the spirit and scope thereof, as encompassed in the accompanying claims. Therefore, it is intended in the appended claims to cover all such equivalent variations which do essentially the same thing in essentially the same way to produce the same result as those equivalent variations come within the scope of the invention as described.

What is claimed is:

1. An improved artificial denture for providing a cosmetic improvement in the facial appearance of a denture user who has at least one depressed area in a surface of the user's face, the depressed area being an age line, the depressed area being located in an area overlying the denture when the denture is in such use, and wherein the at least one depressed area lies generally on a line between a point adjacent a nostril on one side of the face of the user and a point adjacent a corner of the user's mouth on said one side of the user's face, the improved denture comprising;

at least one protuberance means for stretching and supporting the at least one depressed age line area of the user's face, said protuberance means being located in a predetermined location in a gum area of the denture and being located above and between a first bicuspid and a second molar of the denture said protuberance being generally in a line for underlying said at least one age line.

2. A method for improving the facial appearance of a person who has at least one depressed facial area, the at least one depressed area being an age line which begins at a point generally adjacent a nostril on one side of the person's face and ends at a point generally adjacent a corner of the person's mouth on said one side of the person's face, the age line overlying a gum area of an artificial denture which is adapted for placement in a normal position in the person's mouth, the method comprising the step of:

shaping the denture to provide at least one protuberance on the denture at a location underlying the at least one depressed area age line when the denture is placed in the normal position within the person's mouth said protuberance being generally in a line underlying said at least one age line.

* * * * *